(12) United States Patent
Manabe et al.

(10) Patent No.: US 8,076,299 B2
(45) Date of Patent: Dec. 13, 2011

(54) METHOD FOR PRODUCING PEPTIDE THIOESTER

(75) Inventors: Shino Manabe, Tokyo (JP); Yukishige Ito, Tokyo (JP); Tomoyuki Sugioka, Tokushima (JP)

(73) Assignee: Riken, Saitama (JP)

( * ) Notice: Subject to any disclaimer, the term of this patent is extended or adjusted under 35 U.S.C. 154(b) by 796 days.

(21) Appl. No.: 12/091,372

(22) PCT Filed: Oct. 25, 2006

(86) PCT No.: PCT/JP2006/321240
§ 371 (c)(1),
(2), (4) Date: Jun. 30, 2008

(87) PCT Pub. No.: WO2007/049635
PCT Pub. Date: May 3, 2007

(65) Prior Publication Data
US 2009/0240034 A1    Sep. 24, 2009

(30) Foreign Application Priority Data

Oct. 25, 2005  (JP) ................................ 2005-309853

(51) Int. Cl.
*A61K 38/16* (2006.01)
*A61K 38/14* (2006.01)
*C10M 135/06* (2006.01)

(52) U.S. Cl. ........ 514/21.3; 514/20.9; 530/324; 508/344
(58) Field of Classification Search ........................ None
See application file for complete search history.

(56) References Cited

U.S. PATENT DOCUMENTS

2003/0191291 A1   10/2003  Kochendoerfer et al.

FOREIGN PATENT DOCUMENTS

| JP | 2004-508338 | | 3/2004 |
| JP | 2004-508383 | | 3/2004 |
| WO | 02/20557 | | 3/2002 |
| WO | 03/070764 | * | 8/2003 |

OTHER PUBLICATIONS

He, Organic Letters, 2006, 8, 2483-2485.*
Kerber, 1968, The journal of Organic Chemistry, 33, 4442-4445.*
English Traslation of JP 2007/049635, Traslation date: Aug. 9, 2011.*
English Traslation of Foreign priority document: Japan 2005-30953 Oct. 25, 2005 filed on Aug. 18, 2011 by applicants.*
Ten Holte et al., "Solid-Phase Synthesis of 3,5-Disubstituted 1,3-Oxazolidin-2-ones by an Activation/Cyclo-elimination Process", *Tetrahedron Lett.*, vol. 39, pp. 7407-7410 (1998).
Li et al., "Direct Preparation of Peptide Thioesters Using an Fmoc Solid-Phase Method", *Tetrahedron Lett.*, vol. 39, pp. 8669-8672 (1998).
Ingenito et al., "Solid-Phase Synthesis of Peptide C-Terminal Thioesters by Fmoc/t-Bu Chemistry", *J. Am. Chem. Soc.*, vol. 121, pp. 11369-11374 (1999).
Sewing et al., "Fmoc-Compatible Solid-Phase Peptide Synthesis of Long C-Terminal Peptide Thioesters", *Angew. Chem. Int. Ed.*, vol. 40, No. 18, pp. 3395-3396 (2001).
Brask et al., "Fmoc Solid-Phase Synthesis of Peptide Thioesters by Masking as Trithioortho Esters", *Org. Lett.*, vol. 5, pp. 2951-2953 (2003).
Botti et al., "Native Chemical Ligation through in Situ O to S Acyl Shift", *Org. Lett.*, vol. 6, pp. 4861-4864 (2004).
Ollivier et al., "Fmoc Solid-Phase Synthesis of Peptide Thioesters Using an Intramolecular N,S-Acyl Shift", *Org. Lett.*, vol. 7, pp. 2647-2650 (2005).

* cited by examiner

*Primary Examiner* — Cecilia J Tsang
*Assistant Examiner* — Satyanarayana Gudibande
(74) *Attorney, Agent, or Firm* — Greenblum & Bernstein, P.L.C.

(57) ABSTRACT

It is an object of the present invention to provide a novel method for producing a peptide thioester. In the present invention, general peptide synthesis is performed on a solid-phase resin, carboxylic acid obtained after cutout is allowed to react with p-toluenesulfonyl isocyanate, and then the reaction product is alkylated, and is reacted with thiol. Thus, peptide thioester is simply synthesized under mild conditions.

12 Claims, No Drawings

METHOD FOR PRODUCING PEPTIDE THIOESTER

TECHNICAL FIELD

The present invention relates to a method for producing a peptide thioester.

BACKGROUND ART

In recent years, it has been shown that, with regard to peptide synthesis, a block synthesis method or a chemical native ligation method is effective for the synthesis of a long chain peptide. In both the aforementioned methods, a peptide thioester is essential.

Examples of known thioester synthesis methods using an Fmoc solid-phase peptide synthesis method include: a method of deprotecting an Fmoc group using a weak base instead of piperidine (Direct Preparation of Peptide Thioesters Using an Fmoc Solid-Phase Method, X. Li, T. Kawakami, S. Aimoto, Tetrahedron Lett., 1998, 39, 8660-8672); a method using a Safety Catch linker of Kenner (it has been known that this method involves difficulty in introduction of the linker into a resin or introduction or cutout of the first amino acid residue, and thus this method has been applied to only a limited range.) (Solid-Phase Synthesis of Peptide C-Terminal Thioesters by Fmoc/tBu Chemistry, R. Ingenito, E. Bianchi, D. Fattori, A. Pessi, J. Am. Chem. Soc., 1999, 121, 11369-11374); a method which comprises extending a peptide chain by the Fmoc method, cutting it out, and then converting carboxylic acid to a thioester using $Me_2AlCl$-thiol (there are cases where a functional group of amino acid side chain is impaired.) (Fmoc-Compatible Solid-Phase Peptide Synthesis of Long C-Terminal Peptide Thioesters, A. Sewing, D. Hilvert, Angew. Chem. Int. Ed., 2001, 40, 3395-3398); and a method of protecting thiol (this method is disadvantageous in that it can be applied only to Gly, and in that a side chain protecting group cannot be selectively deprotected.) (Fmoc Solid-Phase Synthesis of Peptide Thioesters by Masking as Trithioorthoesters, J. Brask, F. Albericio, K. J. Jensen, Org. Lett., 2003, 5, 2951-2953). In addition, a publication (Native Chemical Ligation through in Situ 0 to S Acyl Shift, P. Botti, M. Villan, S. Manganinello, H. Gaertner, Org. Lett., 2004, 6, 4861-4864) describes a method, which comprises introducing a residue having an ester bond that has a protected thiol group on the side chain, conducting a peptide elongation reaction in the solid phase, eliminating a protecting group from the thiol group after cutting it out, so as to cause an O- to S acyl shift in a molecule, thereby synthesizing a thioester. However, the stability of an ester portion under basic conditions during deprotection of Fmoc in such an Fmoc solid-phase peptide synthesis is unknown. Moreover, another publication (Fmoc-Solid-Phase Synthesis of Peptide Thioesters Using an Intramolecular N, S-Acyl Shift, N. Ollivier, J-B. Behr, O. El-Mahdi, A. Blanpain, O. Melnyk, Org. Lett., 2005, 7, 2647-2650) describes a method which comprises performing alkylation on nitrogen via a Mitsunobu reaction by using alcohol having a protected thiol group, and then deprotecting the protecting group of the thiol group, so as to synthesize a thioester by an acyl shift to thiol in a molecule. However, this method is problematic in terms of the yield of the Mitsunobu reaction.

DISCLOSURE OF THE INVENTION

Problems to be Solved by the Invention

In the Fmoc method that is currently mainly applied to peptide synthesis, when a solid-phase resin is allowed to bind to a peptide via a thioester, there has been a difficulty in peptide synthesis because a thioester portion is weak to bases. It is an object of the present invention to provide a novel method for producing a peptide thioester, which solves the aforementioned problems.

Means for Solving the Problems

The present inventors have conducted intensive studies directed towards achieving the aforementioned object. The present inventors have succeeded in developing a method for simply synthesizing a thioester under mild conditions, which comprises performing general peptide synthesis on a solid-phase resin with a linker (a chlorotrityl linker, etc.) which is commonly used in the Fmoc method, allowing carboxylic acid obtained after cutout to react with p-toluenesulfonyl isocyanate, alkylating the reaction product, and then allowing the resultant to react with thiol. Thus, the present invention has been completed.

That is to say, in the present invention, a peptide that can be synthesized by a common Fmoc method is cut out of a solid phase, and C-terminal carboxylic acid is then allowed to react with p-toluenesulfonyl isocyanate in the presence of a base (triethylamine, diisopropylethylamine, etc.) to obtain tosylamide. Thereafter, the obtained tosylamide is alkylated with iodoacetonitrile or iodomethane on a nitrogen atom for activation to a nucleophile, and it is then allowed to react with thiols, thereby converting it to a thioester. In addition, the present inventors have also found that such an alkylation reaction on a nitrogen atom can be significantly accelerated by application of microwave. Moreover, the alkylation can also be carried out via a Mitsunobu reaction under neutral conditions. The reaction in the method of the present invention progresses under mild conditions, and does not impair side chain functional groups. Furthermore, since the thus synthesized peptide can be reacted with various thiols, a thioester alkyl portion or aryl portion can be easily modified. As a peptide used to synthesize a thioester, a chemically synthesized peptide may be used, or a peptide or protein isolated from a living body may also be used. Otherwise, a glycopeptide may also be used.

That is, the present invention provides a method for producing a thioester of a peptide or a glycopeptide, which comprises:

(1) a step of allowing a peptide or glycopeptide having a protected amino group at the N-terminus and a carboxyl group at the C-terminus to react with a compound represented by the formula $R-SO_2-N=C=O$ (wherein R represents an alkyl group containing 1 to 10 carbon atoms, or an aryl group that may have a substituent) in the presence of a base, so as to synthesize a peptide or glycopeptide having a protected amino group at the N-terminus and —CONH—$SO_2$—R (wherein R has the same definitions as described above) at the C-terminus;

(2) a step of allowing a peptide or glycopeptide having a protected amino group at the N-terminus and —CONH—$SO_2$—R (wherein R has the same definitions as described above) at the C-terminus to react with a compound represented by the formula Hal-$CH_2$—X (wherein Hal represents a halogen atom, and X represents a hydrogen atom, —CN, or —$CO_2R^1$ wherein $R^1$ represents an alkyl group containing 1 to 10 carbon atoms) in the presence of a base, or allowing the aforementioned peptide or glycopeptide to react with trimethylsilyldiazomethane or $Me_3O.BF_4$, so as to synthesize a peptide or glycopeptide having a protected amino group at the N-terminus and —CON(CH$_2$X)—SO$_2$—R (wherein X and R have the same definitions as described above) at the C-terminus; and (3) a step of allowing a peptide or glycopeptide having a protected amino group at the N-terminus and —CON(CH$_2$X)—SO$_2$—R (wherein X and R have the same definitions as described above) at the C-terminus to react with a compound represented by the formula Y—SH (wherein Y represents an alkyl group containing 1 to 10 carbon atoms, an alkenyl group containing 2 to 10 carbon atoms, an alkynyl group containing 2 to 10 carbon atoms, an aryl group, or a group formed by the combination thereof, and these groups may have a substituent) in the presence of a base, so as to synthesize a peptide or glycopeptide having a protected amino group at the N-terminus and —CO—S—Y (wherein Y has the same definitions as described above) at the C-terminus.

Preferably, the peptide or glycopeptide having a protected amino group at the N-terminus and a carboxyl group at the C-terminus is a peptide synthesized by solid-phase synthesis.

Preferably, the peptide has a length of 2 to 50 amino acid residues.

Preferably, the protecting group for the amino group is 9-fluorenylmethyloxycarbonyl (Fmoc), t-butyloxycarbonyl (Boc), or benzyloxycarbonyl (Cbz).

Preferably, the base used in steps (1) to (3) is a tertiary amine or an inorganic base.

Preferably, the compound represented by the formula R—SO$_2$—N=C=O is p-toluenesulfonyl isocyanate.

Preferably, the compound represented by the formula Hal-CH$_2$—X is iodomethane (CH$_3$I) or iodoacetonitrile (ICH$_2$CN).

Preferably, the compound represented by Y—SH is benzyl mercaptan, HS(CH$_2$)$_9$COOCH$_3$, or HSCH$_2$P(C$_6$H$_5$)$_2$.

BEST MODE FOR CARRYING OUT THE INVENTION

The embodiments of the present invention will be described in detail below.

The method of the present invention comprises: a step of allowing a peptide or glycopeptide (carboxylic acid) having a protected amino group at the N-terminus and a carboxyl group at the C-terminus to react with a compound such as p-toluenesulfonyl isocyanate (step 1); an alkylation step (step 2); and a step of allowing the resultant to react with thiol (step 3). Steps 1 to 3 will be successively described below.

(1) Step 1

Step 1 is a step of allowing a peptide or glycopeptide having a protected amino group at the N-terminus and a carboxyl group at the C-terminus to react with a compound represented by the formula R—SO$_2$—N=C=O (wherein R represents an alkyl group containing 1 to 10 carbon atoms, or an aryl group that may have a substituent) in the presence of a base, so as to synthesize a peptide or glycopeptide having a protected amino group at the N-terminus and —CONH—SO$_2$—R (wherein R has the same definitions as described above) at the C-terminus.

The peptide or glycopeptide used in the present invention is a peptide or glycopeptide having a protected amino group at the N-terminus and a carboxyl group at the C-terminus. The aforementioned peptide or glycopeptide may be either a chemically synthesized peptide (solid-phase synthesis, etc.), or a natural peptide or protein isolated from a living body. In the present invention, a glycopeptide may also be used. An O-bound glycopeptide is present in the form of a repeated structure at the terminus of RNA polymerase II in a living body, and it plays an important role in a transcription process. Moreover, it has been pointed out that the role of a GlcNAc sugar chain is associated with signal transduction or diabetes. The term "peptide" is used in the present invention to include a glycopeptide. The length of a peptide is not particularly limited. Any type of peptide can be used, as long as it comprises two or more amino acid residues. The length of the peptide is preferably between approximately 2 to 50 amino acid residues.

The type of the protecting group for the amino group of the peptide is not particularly limited. Protecting groups known to persons skilled in the art can be used. Specific examples of the protecting group for the amino group may include 9-fluorenylmethyloxycarbonyl (Fmoc), benzyloxycarbonyl (Cbz), t-butyloxycarbonyl (Boc), and p-biphenylisopropyloxycarbonyl. Particularly preferably, 9-fluorenylmethyloxycarbonyl (Fmoc), t-butyloxycarbonyl (Boc), or benzyloxycarbonyl (Cbz) may be used.

In step 1, the aforementioned peptide or glycopeptide is allowed to react with a compound represented by the formula R—SO$_2$—N=C=O (wherein R represents an alkyl group containing 1 to 10 carbon atoms, or an aryl group that may have a substituent) in the presence of a base, so as to synthesize a peptide or glycopeptide having a protected amino group at the N-terminus and —CONH—SO$_2$—R at the C-terminus.

The alkyl group containing 1 to 10 carbon atoms represented by R may be a linear or branched alkyl group. Examples of the alkyl group may include a methyl group, an ethyl group, a propyl group, an isopropyl group, a butyl group, an isobutyl group, a sec-butyl group, a tert-butyl group, a pentyl group, a tert-pentyl group, a hexyl group, a heptyl group, an octyl group, a nonyl group, and a decyl group.

Examples of the aryl group that may have a substituent may include a phenyl group and a naphthyl group. An example of the substituent that the aryl group may have may be the aforementioned alkyl group containing 1 to 10 carbon atoms, and the number of such substituents may be one or two or more.

A particularly preferred specific example of the compound represented by the formula R—SO$_2$—N=C=O may be p-toluenesulfonyl isocyanate.

Specific examples of the base used in step 1 may include a tertiary amine and an inorganic base. A weak base is preferable. Specific examples of the tertiary amine may include triethylamine and diisopropylethylamine. Specific examples of the inorganic base may include potassium carbonate, sodium carbonate, potassium hydroxide, and sodium hydroxide.

In step 1, a compound represented by the formula R—SO$_2$—N=C=O, such as p-toluenesulfonyl isocyanate, is added dropwise to a solution containing a peptide or glycopeptide and a base such as triethylamine in a suitable solvent (e.g. THF). The mixture is stirred at room temperature in N$_2$ atmosphere, and N,N'-dimethyl-1,3-propanediamine is then added to the mixture, so as to destroy excessive isocyanate. Subsequently, the mixture is diluted with CHCl$_3$ or the like, and it is then washed with a hydrochloric acid aqueous solution. Thereafter, an aqueous layer is extracted with CHCl$_3$. The combined layer is washed and is then dried. The solvent is distilled away under reduced pressure, and the residue is purified by silica gel column chromatography, so as to obtain a reaction product that is a peptide or glycopeptide having a protected amino group at the N-terminus and —CONH—SO$_2$—R at the C-terminus. This reaction product is subjected to the reaction of the following step 2.

(2) Step 2

Step 2 is a step of allowing a peptide or glycopeptide having a protected amino group at the N-terminus and —CONH—SO$_2$—R (wherein R has the same definitions as described above) at the C-terminus to react with a compound represented by the formula Hal-CH$_2$—X (wherein Hal represents a halogen atom, and X represents a hydrogen atom, —CN, or —CO$_2$R$^1$ wherein R$^1$ represents an alkyl group containing 1 to 10 carbon atoms) in the presence of a base, or allowing the aforementioned peptide or glycopeptide to react with trimethylsilyldiazomethane or Me$_3$O.BF$_4$, so as to synthesize a peptide or glycopeptide having a protected amino group at the N-terminus and —CON(CH$_2$X)—SO$_2$—R (wherein X and R have the same definitions as described above) at the C-terminus.

In the formula Hal-CH$_2$—X, Hal represents a halogen atom, and X represents a hydrogen atom, —CN, or —CO$_2$R$^1$, wherein R$^1$ represents an alkyl group containing 1 to 10 carbon atoms. Examples of the halogen represented by Hal may include fluorine, chlorine, bromine, and iodine. Of these, iodine is particularly preferable. The alkyl group containing 1 to 10 carbon atoms represented by R$^1$ may be a linear or branched alkyl group. Examples of the alkyl group may include a methyl group, an ethyl group, a propyl group, an isopropyl group, a butyl group, an isobutyl group, a sec-butyl group, a tert-butyl group, a pentyl group, a tert-pentyl group, a hexyl group, a heptyl group, an octyl group, a nonyl group, and a decyl group.

Specific examples of the compound represented by the formula Hal-CH$_2$—X may include iodomethane (CH$_3$I) and iodoacetonitrile (ICH$_2$CN).

Specific examples of the base used in step 2 may include a tertiary amine and an inorganic base. A weak base is preferable. Specific examples of the tertiary amine may include triethylamine and diisopropylethylamine. Specific examples of the inorganic base may include potassium carbonate, sodium carbonate, potassium hydroxide, and sodium hydroxide. The base used in step 2 may be identical to or different from the base used in step 1.

In step 2, a compound represented by the formula Hal-CH$_2$—X (e.g. iodomethane, iodoacetonitrile, etc.) and a base are added to a solution containing a peptide or glycopeptide having —CONH—SO$_2$—R (e.g. a tosylamide group) at the C-terminus which is a product obtained in step 1 in a suitable solvent (e.g. DMF, etc.). The mixture is reacted at a predetermined temperature for a certain period of time. (Such a predetermined temperature is not particularly limited, as long as the reaction progresses at the temperature. The temperature is, for example, between 50° C. and 70° C.) Thereafter, 10% citric acid aqueous solution and CHCl$_3$ are added to the mixture. After separation, an aqueous phase is extracted with CHCl$_3$. The combined phase is washed and is then dried. The solvent is distilled away under reduced pressure, and the residue is purified by silica gel column chromatography, so as to obtain a reaction product that is a peptide or glycopeptide having a protected amino group at the N-terminus and —CON(CH$_2$X)—SO$_2$—R (wherein X and R have the same definitions as described above) at the C-terminus. This reaction product is subjected to the reaction of the following step 3.

(3) Step 3

Step 3 is a step of allowing a peptide or glycopeptide having a protected amino group at the N-terminus and —CON(CH$_2$X)—SO$_2$—R (wherein X and R have the same definitions as described above) at the C-terminus to react with a compound represented by the formula Y—SH (wherein Y represents an alkyl group containing 1 to 10 carbon atoms, an alkenyl group containing 2 to 10 carbon atoms, an alkynyl group containing 2 to 10 carbon atoms, an aryl group, or a group formed by the combination thereof, and these groups may have a substituent) in the presence of a base, so as to synthesize a peptide or glycopeptide having a protected amino group at the N-terminus and —CO—S—Y (wherein Y has the same definitions as described above) at the C-terminus.

In the formula Y—SH, Y represents an alkyl group containing 1 to 10 carbon atoms, an alkenyl group containing 2 to 10 carbon atoms, an alkynyl group containing 2 to 10 carbon atoms, an aryl group, or a group formed by the combination thereof, and these groups may have a substituent. The alkyl group containing 1 to 10 carbon atoms represented by Y may be a linear or branched alkyl group. Examples of the alkyl group may include a methyl group, an ethyl group, a propyl group, an isopropyl group, a butyl group, an isobutyl group, a sec-butyl group, a tert-butyl group, a pentyl group, a tert-pentyl group, a hexyl group, a heptyl group, an octyl group, a nonyl group, and a decyl group. Examples of the alkenyl group containing 2 to 10 carbon atoms and the alkynyl group containing 2 to 10 carbon atoms, which are represented by Y, may include groups formed by substituting a single bond in the aforementioned alkyl group (except for a methyl group) with a double bond or a triple bond. The number of the double bond or triple bound may be one or two or more. Examples of the aryl group represented by Y may include a phenyl group and a naphthyl group. Y may also be a group formed by the combination among an alkyl group containing 1 to 10 carbon atoms, an alkenyl group containing 2 to 10 carbon atoms, an alkynyl group containing 2 to 10 carbon atoms, and an aryl group. A specific example of the group formed by such a combination may be a benzyl group (C$_6$H$_5$—CH$_2$—) formed by the combination of a methyl group with a phenyl group. In addition, the group represented by Y, such as an alkyl group, may have a substituent. Examples of the substituent may include, but are not limited to, COOCH$_3$ and a —P(C$_6$H$_5$)$_2$ group.

Specific examples of the compound represented by the formula Y—SH may include benzyl mercaptan, HS(CH$_2$)$_9$COOCH$_3$, and HSCH$_2$P(C$_6$H$_5$)$_2$.

Specific examples of the base used in step 3 may include a tertiary amine and an inorganic base. A weak base is preferable. Specific examples of the tertiary amine may include triethylamine and diisopropylethylamine. Specific examples of the inorganic base may include potassium carbonate, sodium carbonate, potassium hydroxide, and sodium hydroxide. The base used in step 3 may be identical to or different from the base used in step 1 or 2.

In step 3, a base and a compound represented by the formula Y—SH (e.g. benzyl mercaptan, etc.) are added to a solution containing a peptide or glycopeptide having —CON(CH$_2$X)—SO$_2$—R at the C-terminus which is a product obtained in step 2 in a suitable solvent (e.g. DMF, etc.) at room temperature. The mixture is reacted at room temperature in N$_2$ atmosphere for a certain period of time. Thereafter, a 10% citric acid aqueous solution and CHCl$_3$ are added to the mixture. After separation, an aqueous phase is extracted with CHCl$_3$. The combined phase is washed and is then dried. The solvent is distilled away under reduced pressure, and the residue is purified by silica gel column chromatography, so as to obtain a reaction product that is a peptide or glycopeptide having a protected amino group at the N-terminus and —CO—S—Y (wherein Y has the same definitions as described above) at the C-terminus.

The present invention will be further specifically described in the following examples. However, these examples are not intended to limit the scope of the present invention.

EXAMPLES

(1) Fmoc Method

A resin was washed with NMP (N-methylpyrrolidone) for 1 minute (twice), and it was then treated with an NMP solution of 25% piperidine for 5 minutes, and then for 10 minutes.

Amino acid on a resin, Fmoc amino acid, HOBt, HBTU, and DIEA (diisopropylethylamine) were reacted at a molar ratio of 1:4:4:3.6:8. Fmoc amino acid, HOBt, and HBTU were dissolved in NMP, and DIEA was then added to the solution. The obtained mixture was stirred for 1 to 3 minutes, and it was then added to the resin, followed by stirring for 1 hour.

Approximately 20 ml of an NMP solution that contained HOBt, acetic anhydride and DIEA was added to 1 g of the resin, and the obtained mixture was then stirred for 10 minutes. A color reaction was carried out by a ninhydrin test or the like, so as to confirm that there were no unreacted amino groups. Thereafter, the routine proceeded to an operation to eliminate the Fmoc group.

(2) Obtainment of Protected Peptide From 2-Chlorotrityl Resin

A DCM (dichloromethane) solution of 25% hexafluoroisopropyl alcohol was added to a fully dried protected peptide resin, and the mixture was then stirred for 60 minutes. Thereafter, the resin was separated by filtration and was then washed with a DCM solution of HFIP. The filtrate was mixed with the washing solution, and the obtained solution was concentrated under reduced pressure. Thereafter, water, ether, or the like was added to the residue to precipitate the peptide, so as to obtain a crude peptide (for example, Boc-Trp-Ser(t-Bu)-His(Trt)-Trp(Boc)-Ser(t-Bu)-Pro-OH).

(3) Peptide Synthesis by Liquid Phase Method

A Boc peptide and a Cbz peptide were synthesized in a liquid phase. In addition, in the case of a solid-phase reaction, a Boc peptide and a Cbz peptide can be synthesized by synthesizing a peptide by the Fmoc method and then adding Boc amino acid or Cbz amino acid to the final peptide.

BocThr(Bn)OH+H-Gly-OBn→BocThr(Bn)-Gly-OBn

EDC (950 mg, 4.96 mmol) and HOBt (670 mg, 4.96 mmol) were added to a CH$_2$Cl$_2$ solution containing acid (1.77 g, 4.96 mmol) and amine (1.0 g, 4.96 mmol) at room temperature. 30 minutes later, water was added to the mixture. After separation, an aqueous phase was extracted with CHCl$_3$, and the combined phase was washed with a saline solution. The extract was dried over Na$_2$SO$_4$, and the solvent was then distilled away under reduced pressure. The residue was purified by silica gel column chromatography (5% MeOH/CHCl$_3$).

BocThr(Bn)-Gly-OBn→BocThr(Bn)-Gly-OH

A CH$_2$Cl$_2$ suspension (5 ml) containing t-BuMe$_2$SiH (0.27 ml, 1.65 mmol), Pd(OAc)$_2$ (12.3 mg, 0.055 mmol) and Et$_3$N (0.25 ml, 1.76 mmol) was stirred at room temperature in N$_2$ atmosphere. 15 minutes later, a CH$_2$Cl$_2$ solution of a benzyl ester (500 mg, 1.10 mmol) was added to the mixture. Two days later, a saturated NH$_4$Cl aqueous solution was added to the mixture. After separation, an aqueous phase was extracted with ether, and the combined phase was washed with a saline solution. The extract was dried over Na$_2$SO$_4$, and the solvent was then distilled away under reduced pressure. The residue was purified by silica gel column chromatography (5% ethyl acetate/hexane).

(4) Synthesis of Tosylamide

Example 1 p-toluenesulfonyl isocyanate (0.18 ml, 1.21 mmol) was added dropwise to a THF solution (5 ml) containing acid (BocThr(Bn)-Gly-OH) (402 mg, 1.10 mmol) and triethylamine (0.18 ml, 1.32 mmol). The mixture was stirred at room temperature for 30 minutes in N$_2$ atmosphere. Thereafter, N,N'-dimethyl-1,3-propanediamine (0.1 ml) was added to the reaction solution, so as to destroy excessive isocyanate. 10 minutes later, the mixture was diluted with CHCl$_3$, and it was then washed with a 1 M HCl aqueous solution. An aqueous phase was extracted with CHCl$_3$. The combined phase was washed with a saline solution. The extract was dried over Na$_2$SO$_4$, and the solvent was then distilled away under reduced pressure. The residue was purified by silica gel column chromatography (10% MeOH/CHCl$_3$).

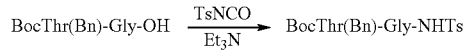

91%; $^1$H-NMR δ 7.78 (2H, d, J=8.8 Hz), 7.15-7.41 (7H, m), 6.77 (1H, br. s), 5.30 (1H, br. s), 4.53 (1H, d, J=11.2 Hz), 4.38 (1H, d, J=11.2 Hz), 4.11 (1H, m), 4.04 (1H, m), 3.80 (1H, dd, J=5.6, 12.4 Hz), 3.75 (1H, dd, J=5.6, 12.4 Hz), 3.65 (1H, m), 2.31 (3H, s), 1.36 (9H, s), 1.10 (3H, d, J=6.8 Hz), [α]$^{27}_D$+ 54.0 (c 1.0 CHCl$_3$), MS (TOF) m/z 531 (M$^+$+Na), calcd for C$_{27}$H$_{29}$N$_3$O$_7$S C, 57.79; H, 6.40; N, 8.09. found for C, 57.52; H, 6.38; N, 8.05

Example 2 p-toluenesulfonyl isocyanate (0.010 ml, 0.055 mmol) was added dropwise to a THF solution (0.10 ml) containing acid (BocTrp-Ser(t-Bu)-His(Trt)-Trp(Boc)-Ser(t-Bu)-Pro-OH) (68.3 mg, 0.050 mmol) and triethylamine (0.010 ml, 0.055 mmol). The mixture was stirred at room temperature for 30 minutes in N$_2$ atmosphere. Thereafter, N,N'-dimethyl-1,3-propanediamine (0.1 ml) was added to the reaction solution, so as to destroy excessive isocyanate. 10 minutes later, the mixture was diluted with CHCl$_3$, and it was then washed with a 1 M HCl aqueous solution. An aqueous phase was extracted with CHCl$_3$. The combined phase was washed with a saline solution. The extract was dried over Na$_2$SO$_4$, and the solvent was then distilled away under reduced pressure. The residue was purified by silica gel column chromatography (10% MeOH/CHCl$_3$).

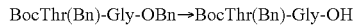

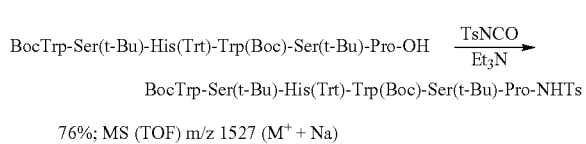

76%; MS (TOF) m/z 1527 (M$^+$ + Na)

Example 3

Carboxylic acid (108 mg, 0.071 mmol) and triethylamine (0.012 ml, 0.085 mmol) were dissolved in THF (0.40 ml), and p-toluene isocyanate (0.012 ml, 0.079 mmol) was then added dropwise to the solution. The mixed solution was stirred at room temperature for 30 minutes in a nitrogen atmosphere. Thereafter, N,N'-dimethyl-1,3-propanediamine (0.1 ml) was added to the reaction solution, and the mixture was then stirred for 10 minutes, so as to destroy excessive isocyanate. The mixture was diluted with chloroform, and it was then washed with 1 M HCl. An aqueous phase was extracted with chloroform. The combined organic phase was washed with a saturated saline solution. The combined organic phase was dried over $Na_2SO_4$, and the solvent was then concentrated under reduced pressure. The residue was purified by silica gel column chromatography (hexane:ethyl acetate=1:4), so as to obtain tosylamide in a quantitative manner.

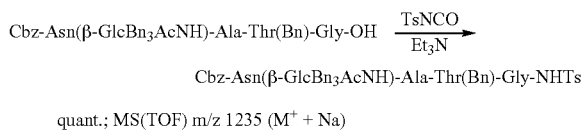

quant.; MS(TOF) m/z 1235 ($M^+$ + Na)

(5) Synthesis of N-Alkyltosylamide

Example 1

Iodoacetonitrile (0.20 ml, 2.8 mmol) and potassium carbonate (58 mg, 0.42 mmol) were added at 60° C. to a DMF solution (3.0 ml) containing tosylamide (147 mg, 0.28 mmol). 12 hours later, a 10% citric acid aqueous solution and $CHCl_3$ were added to the mixture. After separation, an aqueous phase was extracted with $CHCl_3$, and the combined phase was washed with a saline solution. The extract was dried over $Na_2SO_4$, and the solvent was then distilled away under reduced pressure. The residue was purified by silica gel column chromatography (50% ethyl acetate/hexane).

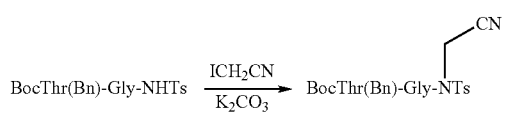

51%; $^1$H-NMR δ 7.87 (2H, d, J=7.2 Hz), 7.42 (2H, d, J=7.2 Hz), 7.23-7.35 (5H, m), 7.13 (1H, br. s), 5.41 (1H, br. s), 4.64 (2H, s), 4.58 (1H, d, J=11.2 Hz), 4.52 (1H, d, J=11.2 Hz), 4.48 (2H, m), 4.27 (1H, m), 4.17 (1H, m), 2.45 (3H, s), 1.43 (9H, s), 1.19 (3H, d, J=5.6 Hz)

Example 2

Iodomethane (1.24 ml, 19.9 mmol) and potassium carbonate (411 mg, 2.98 mmol) were added at room temperature to a DMF solution (15 ml) containing tosylamide (750 mg, 1.99 mmol). 10 minutes later, a 10% citric acid aqueous solution and $CHCl_3$ were added to the mixture. After separation, an aqueous phase was extracted with $CHCl_3$, and the combined phase was washed with a saline solution. The extract was dried over $Na_2SO_4$, and the solvent was then distilled away under reduced pressure. The residue was purified by silica gel column chromatography (60% ethyl acetate/hexane).

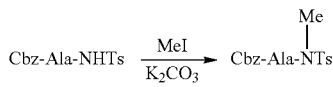

quant.; $^1$H-NMR δ 7.89 (2H, d, J=8.0 Hz), 7.34 (7H, m), 5.34 (1H, br.s), 5.05 (1H, t, J=6.8 Hz), 3.19 (3H, s), 2.68 (3H, s), 1.43 (3H, d, J=6.8 Hz)

Example 3

A trimethylsilyldiazomethane solution (17 μl; 2 M in hexane) was added at room temperature to a solution containing sulfonamide (25.5 mg, 17 μmol) in PhH and MeOH (0.5 ml, 1:1). The mixture was stirred at room temperature for 10 minutes, and the solvent was then distilled away under reduced pressure. The residue was purified by silica gel column chromatography.

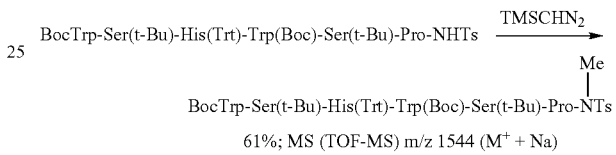

61%; MS (TOF-MS) m/z 1544 ($M^+$ + Na)

Example 4

A trimethylsilyldiazomethane solution (17 μl, 2 M hexane solution) was added dropwise at room temperature to a benzene-methanol solution (1:1, 0.15 ml) containing sulfonamide (12 mg, 10 μmol). The mixture was stirred at room temperature for 10 minutes, and the solvent was then distilled away under reduced pressure. The residue was purified by silica gel column chromatography.

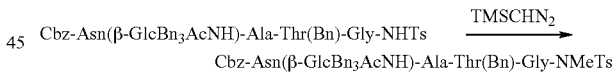

(6) Synthesis of Peptide Thioester

Example 1

Diisopropylethylamine (0.19 ml, 1.1 mmol) and benzyl mercaptan (0.13 ml, 1.1 mmol) were added at room temperature to a DMF solution (1.1 ml) containing N-alkylsulfonamide (62 mg, 0.11 mmol). The mixture was stirred at room temperature for 10 minutes in $N_2$ atmosphere, and a 10% citric acid aqueous solution and $CHCl_3$ were then added to the reaction solution. After separation, an aqueous phase was extracted with $CHCl_3$, and the combined phase was washed with a saline solution. The extract was dried over $Na_2SO_4$, and the solvent was then distilled away under reduced pressure. The residue was purified by silica gel column chromatography.

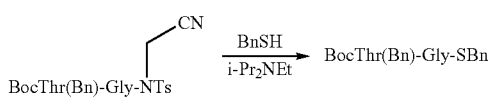

82%; $^1$H-NMR δ 7.23-7.28 (10H, m), 7.10 (1H, br. s), 5.47 (1H, br. s), 4.58 (2H, s), 4.15-4.30 (4H, m), 4.11 (1H, d, J=3.2 Hz), 1.43 (9H, s), 1.19 (3H, d, J=6.4 Hz), $[α]^{30}_D$+29.6 (c 0.32, CHCl$_3$), MS (TOF) m/z 495 (M$^+$+Na), calcd for C$_{27}$H$_{28}$N$_2$O$_5$S C, 63.54; H, 6.82; N, 5.93. found for C, 62.88; H, 6.75; N, 5.77.

Example 2

N-methylsulfonamide (15.9 mg, 0.010 mmol), benzenethiol sodium salt (1.9 mg, 0.015 mmol), and benzyl mercaptan (0.012 ml, 0.10 mmol) were dissolved in DMF (0.10 ml), and the obtained solution was then stirred in a nitrogen atmosphere for 10 minutes. Thereafter, a 10% citric acid aqueous solution was added to the reaction solution, and an aqueous phase was extracted with chloroform several times. An organic phase was dried over Na$_2$SO$_4$, and was then filtrated. The solvent was concentrated under reduced pressure. The residue was purified by silica gel column chromatography. Yield: 25%

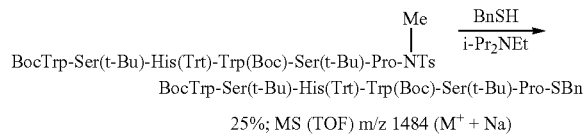

25%; MS (TOF) m/z 1484 (M$^+$ + Na)

Example 3

Benzenethiol sodium salt (1.9 mg, 0.015 mmol) and benzyl mercaptan (0.012 ml, 0.10 mmol) were added at room temperature to a DMF solution (0.15 ml) containing N-methylsulfonamide (12 mg, 0.010 mmol). The mixture was stirred at room temperature in a nitrogen atmosphere for 10 minutes. A 10% citric acid aqueous solution was added to the reaction solution, and an aqueous phase was extracted with chloroform several times. An organic phase was dried over Na$_2$SO$_4$, and was then filtrated. The solvent was concentrated under reduced pressure. The residue was purified by silica gel column chromatography. Yield: 30%

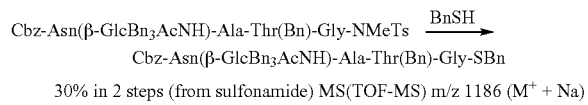

30% in 2 steps (from sulfonamide) MS(TOF-MS) m/z 1186 (M$^+$ + Na)

Example 4

N-alkylsulfonamide (50 mg, 0.12 mmol), diisopropylethylamine (0.031 ml, 0.18 mmol), and methyl 10-mercaptodecanoate (39.4 mg, 0.18 mmol) were dissolved in DMF (0.2 ml), and the obtained solution was then stirred at room temperature in a nitrogen atmosphere for 10 minutes. Thereafter, a 10% citric acid aqueous solution was added to the mixture, and an aqueous phase was extracted with chloroform several times. An organic phase was dried over Na$_2$SO$_4$, and was then filtrated. The solvent was concentrated under reduced pressure. The residue was purified by silica gel column chromatography. Yield: 70%

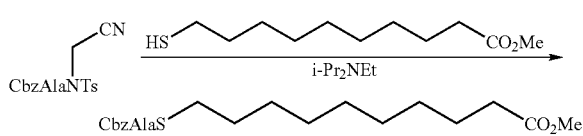

70%; $^1$H-NMR δ 7.23-7.31 (5H, m), 5.19 (1H, m), 5.11 (2H, s), 4.45 (1H, t, J=7.6 Hz), 3.64 (3H, s), 2.85 (2H, t, J=7.2 Hz), 2.28 (2H, t, J=7.2 Hz), 1.54 (4H, m), 1.39 (3H, d, J=7.2 Hz), 1.26 (10H, m), $[α]^{30}_D$-5.39 (c 1.00 CHCl$_3$), MS (TOF) m/z 444(M$^+$+Na), calcd for C$_{22}$H$_{33}$NO$_5$S C, 62.38; H, 7.85; N, 3.31. found for C, 62.11; H, 7.74; N, 3.34

Example 5

N-alkylsulfonamide (50 mg, 0.12 mmol), diisopropylethylamine (0.031 ml, 0.18 mmol), and 2-mercaptomethyldiphenylphosphine (41.9 mg, 0.18 mmol) were dissolved in DMF (0.2 ml), and the obtained solution was then stirred at room temperature in a nitrogen atmosphere for 10 minutes. Thereafter, a 10% citric acid aqueous solution was added to the reaction solution, and an aqueous phase was extracted with chloroform several times. An organic phase was dried over Na$_2$SO$_4$, and was then filtrated. The solvent was concentrated under reduced pressure. The residue was purified by silica gel column chromatography. Yield: 87%

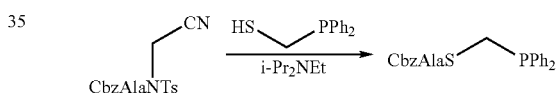

87%; $^1$HNMR δ 7.41-7.36 (5H, m), 7.32-7.30 (10H, m), 5.23 (1H, br.s), 5.07 (2H, s), 4.40 (1H, t, J=7.2 Hz), 3.54-3.42 (2H, m), 1.27 (3H, d, J=7.2 Hz), $^{13}$CNMR δ 199.95 (s), 155.27 (s), 136.56 (s), 136.52 (s), 136.42 (s), 136.38 (s), 135.95 (s), 132.79 (d), 132.73 (s), 132.54 (d), 129.02 (d), 128.60 (s), 128.45 (d), 128.40 (s), 128.38 (d), 128.08 (d), 127.98 (d), 67.09 (t), 56.60 (d), 25.53, 25.29 (t, J=24 Hz), 18.89 (q), $[α]^{30}_D$-31.49 (c 1.00, CHCl$_3$), MS (TOF) m/z 460 (M$^+$+Na), calcd for C$_{24}$H$_{24}$NO$_3$PS C, 65.89; H, 5.53; N, 3.20. found C, 65.79; H, 5.50; N, 3.15.

7) Synthesis of O-Bound Glycopeptide

TMSOTf (0.20 ml, 1.11 mmol) was added dropwise at −78° C. to a solution containing imidate (2.79 g, 4.49 mmol) and Fmoc-Thr-OBn (2.13 mg, 4.94 mmol) in CH$_2$Cl$_2$ (40 ml). After addition of the aforementioned substance, the mixture was stirred at −40° C. overnight. Thereafter, triethylamine (0.2 ml) was added to the reaction solution, and the obtained mixture was then diluted with CHCl$_3$ and saturated NH$_4$Cl. After separation, an aqueous layer was extracted with CHCl$_3$. The combined layer was washed with a saline solution. The extract was dried over Na$_2$SO$_4$, and the solvent was then eliminated by evaporation. The residue was purified by silica gel column chromatography (CHCl$_3$:AcOEt=7:3−1:1), so as to obtain 3.82 g of a product (95%) in the form of a colorless bleb.

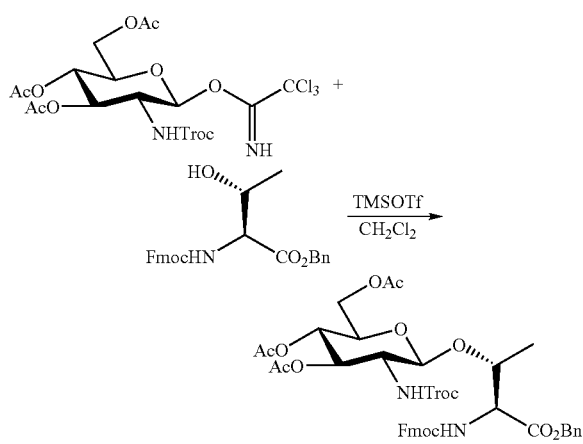

¹H-NMR δ 7.8-7.6 (m, 2H), 7.5 (m, 2H), 7.4-7.24 (m, 9H), 5.74 (m, 1H), 5.14 (d, J=12.0 Hz, 2H), 5.03 (bs, 1H), 4.98 (t, J=9.6 Hz, 1H), 4.56 (m, 2H), 4.50-4.41 (m, 4H), 4.28-4.20 (m, 3H), 4.18 (d, J=4.8 Hz, 1H), 3.51-3.48 (m, 2H), 2.09 (s, 3H), 2.04 (s, 3H), 2.02 (s, 3H), 1.22 (d, J=6.0 Hz, 3H); ¹³C-NMR δ 170.5 (C), 170.4 (C), 169.7 (C), 169.1 (C), 156.6 (C), 153.8 (C), 143.7 (C), 141.1 (C), 135.3 (C), 128.6 (CH), 128.5 (CH), 128.1 (CH), 127.6 (CH), 127.0 (CH), 125.1 (CH), 119.8 (CH), 98.3 (CH), 77.2 (CH), 74.1 (CH), 71.7 (CH), 71.4 (CH), 67.4 (CH$_2$), 61.8 (CH$_2$), 58.6 (CH), 56.4 (CH), 47.2 (CH), 20.8 (CH$_3$), 20.7 (CH$_3$), 17.1 (CH$_3$); [α]$^{24}_D$ −2.0 (c=0.72, CHCl$_3$).

Zn (15 g) was added to a solution containing Troc (2.73 g, 3.06 mmol) in Ac$_2$O (15 ml) and AcOH (30 ml), and the obtained mixture was then intensively stirred for 6 hours. Thereafter, the mixture was filtrated with Celite, and Zn powders were then washed with AcOH and CHCl$_3$ in N$_2$ atmosphere. After evaporation, the residue was purified by silica gel column chromatography (CHCl$_3$:EtOAc=1:1–EtOAc alone), so as to obtain 2.32 g of acetamide (quantitative).

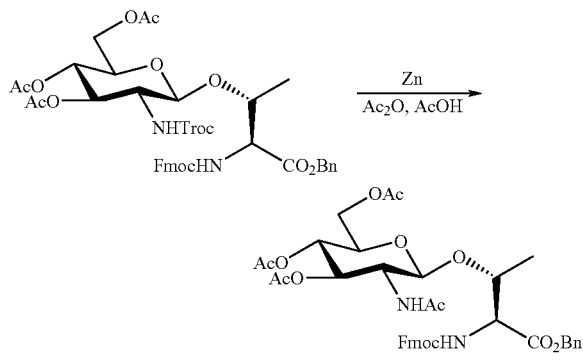

¹H-NMR δ 7.74 (d, J=8.0 Hz, 3H), 7.62 (d, J=7.2 Hz, 2H), 7.4-7.2 (m, 8H), 5.76 (d, J=8.8 Hz, 1H), 5.39 (d, J=7.6 Hz, 1H), 5.28 (t, J=10.8 Hz, 1H), 5.19 (d, J=7.2 Hz, 2H), 4.97 (t, J=9.2 Hz, 1H), 4.64 (d, J=8.0 Hz, 1H), 4.4-4.3 (m, 5H), 4.2-4.0 (m, 4H), 3.65 (m, 1H), 3.45 (m, 1H), 2.02 (s, 3H), 2.01 (s, 3H), 1.98 (s, 3H), 1.92 (s, 3H), 1.19 (d, J=6.1 Hz), ¹³C-NMR δ 170.7, 170.4, 170.1, 169.8, 169.1, 156.6, 143.8, 143.5, 141.1, 135.3, 128.4, 128.3, 128.1, 127.5, 127.0, 126.9, 125.1, 119.8, 98.4, 77.2, 74.4, 71.8, 71.6, 68.4, 67.3, 61.8, 588.7, 55.2, 47.2, 23.5, 20.8, 17.1; [α]$^{24}_D$ −32.4 (c=0.79, CHCl$_3$).

Piperidine (6 ml) was added to a solution containing Fmoc (1.50 g, 1.97 mmol) in DMF (25 ml) at room temperature. 1 hour later, the solvent was eliminated by evaporation. The residue was purified by silica gel column chromatography (CHCl$_3$:MeOH=9:1), and the amino compound was then dissolved in CH$_2$Cl$_2$ (15 ml). After i-Pr$_2$NEt (0.45 ml) and Boc$_2$O (560 mg, 2.57 mmol) had been added to the solution, the mixture was stirred for 3 hours. Thereafter, the mixture was diluted with CHCl$_3$, and it was then washed with 10% citric acid. An aqueous layer was extracted with CHCl$_3$, and the combined layer was washed with a saline solution. The extract was dried over Na$_2$SO$_4$, and the solvent was then eliminated under reduced pressure. The residue was purified by silica gel column chromatography (CHCl$_3$:MeOH=20:1–9:1), so as to obtain 1.25 g of a product (quantitative).

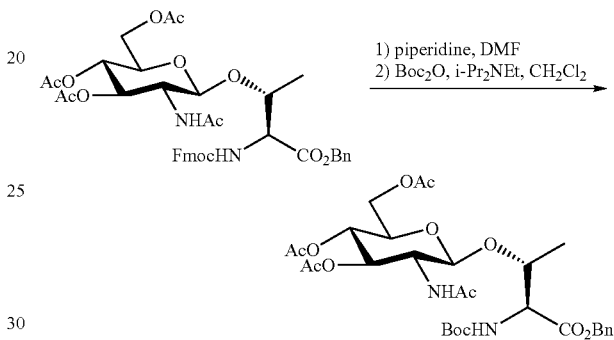

¹H-NMR (CD$_3$OD) δ 7.4-7.3 (m, 5H), 5.19 (t, J=10.8 Hz, 1H), 5.16 (d, J=12.8 Hz, 2H), 4.92 (t, J=9.2 Hz, 1H), 4.62 (d, J=8.8 Hz, 1H), 4.40 (m, 1H), 4.2 (m, 2H), 3.96 (m, 1H), 3.74 (t, J=8.4 Hz, 1H), 3.62 (m, 1H), 1.98 (s, 3H), 1.97 (s, 3H), 1.95 (s, 3H), 1.91 (s, 3H), 1.18 (d, J=6.4 Hz, 3H), ¹³C-NMR δ 173.5 (C), 172.0 (C), 171.5 (C), 171.5 (C), 170.9 (C), 158.1 (C), 137.0 (C), 129.3 (CH), 129.1 (CH), 128.9 (CH), 100.4 (CH), 80.9 (CH), 76.4 (CH), 73.6 (CH), 72.6 (CH), 69.9 (CH), 68.0 (CH$_2$), 63.1 (CH$_2$), 59.9 (CH), 55.5 (CH), 28.7 (CH$_3$), 22.9 (C), 21.7 (CH$_3$), 20.7 (CH$_3$), 20.6 (CH$_3$), 17.6 (CH$_3$); [α]$^{24}_D$ −13.4 (c=1.2, CHCl$_3$).

A solution containing a Bn ester (1.43 g, 2.24 mmol) and 10% Pd/C (150 mg) in methanol (50 ml) was intensively stirred in H$_2$ atmosphere for 30 minutes. After filtration, the catalyst was washed with methanol and CHCl$_3$. After evaporation, a crude product (1.23 g, quantitative) had sufficient purity. Thus, the crude product was directly subjected to the subsequent step without purification.

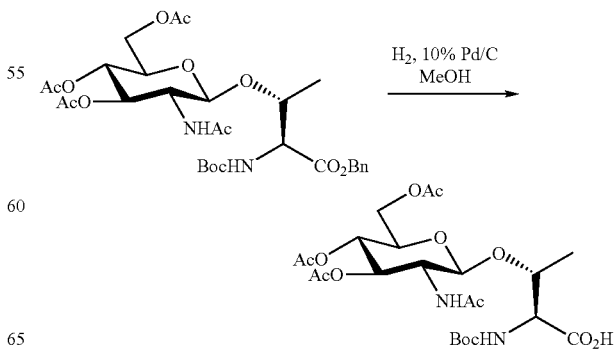

(8) Preparation of Glycopeptide

Liquid-phase peptide synthesis was carried out using the Boc method. Deprotection was carried out using HCl-dioxane, and a peptide bond was formed in the presence of diisopropylethylamine in $CH_2Cl_2$, using WSCDI-HOBt.

(1) Synthesis of Tosylamide

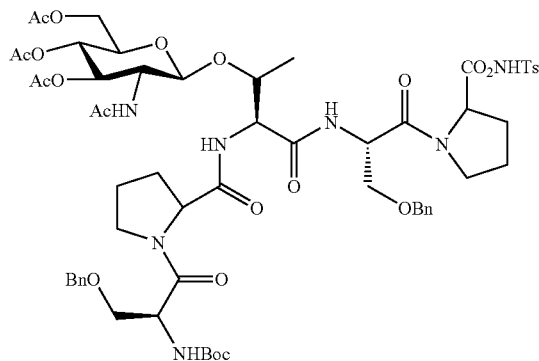

Benzyl ester (100 mg, 0.0842 mmol) and Pd/C (en) (10 mg) were suspended in methanol (1 ml), and the obtained suspension was stirred in a hydrogen atmosphere at room temperature for 8 hours. Thereafter, the catalyst was filtrated with a filter, and was then washed with methanol. The filtrate was distilled away under reduced pressure. The residue was purified by silica gel column chromatography (chloroform:methanol=9:1–7:3), so as to obtain carboxylic acid (91.2 mg) in a quantitative manner. The thus obtained carboxylic acid (75.9 mg, 0.070 mg) was dissolved in THF (0.5 ml). Thereafter, diisopropylethylamine (32 μl, 0.184 mmol) and p-toluenesulfonyl isocyanate (39 μl, 0.256 mmol) were added thereto in an argon atmosphere, and the obtained mixture was stirred for 1 hour. Thereafter, N,N'-dimethyl-1,3-propanediamine (0.1 ml) was added dropwise to the reaction solution, and a 10% citric acid aqueous solution was then added thereto. An aqueous layer was extracted with chloroform. An organic layer was washed with a saline solution, and it was then dried over sodium sulfate. The solvent was distilled away under reduced pressure. The residue was purified by silica gel column chromatography (chloroform:methanol=9:1), so as to obtain 77.5 mg (87%) of tosylamide.

(2) Synthesis of Thioester

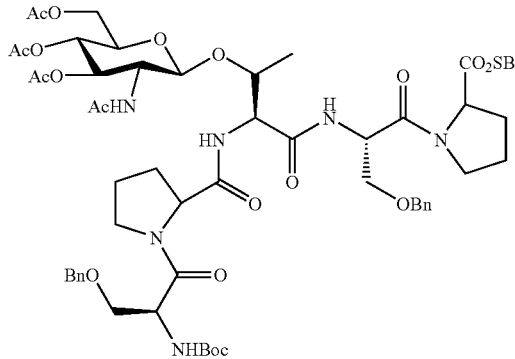

Tosylamide (19.7 mg, 0.0158 mmol) was dissolved in methanol (0.5 ml) and benzene (0.5 ml), and a TMSCHN$_2$ solution (0.5 ml) was then added thereto. The solvent was distilled away under reduced pressure, and it was then immediately dissolved in DMF (0.5 ml). Benzyl mercaptan (19 μl, 0.158 mmol) and diisopropylethylamine (27 μl, 0.158 mmol) were added to the solution. 1 hour later, the reaction solution was directly purified with a molecular sieve column LH20 (methanol), and the obtained product was further purified by silica gel column chromatography (chloroform:methanol=9:1), so as to obtain thioester (10.8 mg, 57%).

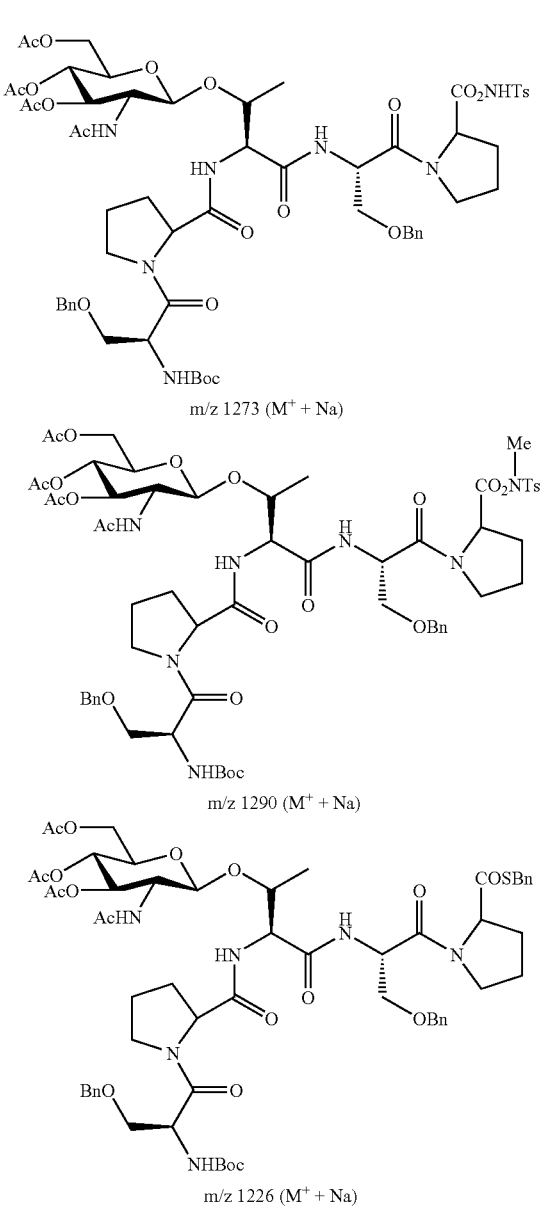

(9) N-Methylation of Tosylsulfonamide using Me$_3$O.Bf$_4$ as a Methylating Agent To a solution containing Cbz-Ala-ONHTs (63.2 mg, 0.168 mmol) in DMF (0.5 ml), i-Pr$_2$NEt (0.24 ml, 1.40 mmol) and Me$_3$O.BF$_4$ (206 mg, 1.40 mmol) were added at room temperature. 10 minutes later, the mixture was diluted with ethyl acetate, and it was then washed with saturated NaHCO$_3$. An aqueous layer was extracted with ethyl acetate. The combined layer was washed with a saline solution. The mixture was dried over Na$_2$SO$_4$, and the solvent was then eliminated by evaporation. The residue was purified by silica gel column chromatography (hexane:AcOEt=7:3), so as to obtain 62.3 mg (95%) of an N-methylated product.

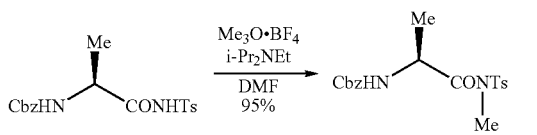

INDUSTRIAL APPLICABILITY

The present invention provides a method for simply synthesizing a peptide having a thioesterified C-terminus under mild conditions. The method of the present invention is advantageous in terms of (1) to (5) described below: (1) a peptide can be synthesized by a common Fmoc method; (2) the operation is simple; (3) reagents are comparatively inexpensive and available; (4) side chain functional groups are not impaired, as far as they are protected; (4) a peptide can be rapidly synthesized; and (5) various modifications can be performed on a thioester alkyl portion or a thioester aryl portion.

The invention claimed is:

1. A method for producing a thioester of a peptide or a glycopeptide, which comprises:
    (1) a step of allowing a peptide or glycopeptide having a protected amino group at the N-terminus and a carboxyl group at the C-terminus to react with a compound represented by the formula R—SO$_2$—N=C=O (wherein R represents an alkyl group containing 1 to 10 carbon atoms, or an aryl group that may have a substituent) in the presence of a base, so as to synthesize a peptide or glycopeptide having a protected amino group at the N-terminus and —CONH—SO$_2$—R (wherein R has the same definitions as described above) at the C-terminus;
    (2) a step of allowing a peptide or glycopeptide having a protected amino group at the N-terminus and —CONH—SO$_2$—R (wherein R has the same definitions as described above) at the C-terminus to react with a compound represented by the formula Hal-CH$_2$—X (wherein Hal represents a halogen atom, and X represents a hydrogen atom, —CN, or —CO$_2$R$^1$ wherein R$^1$ represents an alkyl group containing 1 to 10 carbon atoms) in the presence of a base, or allowing the aforementioned peptide or glycopeptide to react with trimethylsilyldiazomethane or Me$_3$O•BF$_4$, so as to synthesize a peptide or glycopeptide having a protected amino group at the N-terminus and —CON(CH$_2$X)—SO$_2$—R (wherein X and R have the same definitions as described above) at the C-terminus; and
    (3) a step of allowing a peptide or glycopeptide having a protected amino group at the N-terminus and —CON(CH$_2$X)—SO$_2$—R (wherein X and R have the same definitions as described above) at the C-terminus to react with a compound represented by the formula Y—SH (wherein Y represents an alkyl group containing 1 to 10 carbon atoms, an alkenyl group containing 2 to 10 carbon atoms, an alkynyl group containing 2 to 10 carbon atoms, an aryl group, or a group formed by the combination thereof, and these groups may have a substituent) in the presence of a base, so as to synthesize a peptide or glycopeptide having a protected amino group at the N-terminus and —CO—S—Y (wherein Y has the same definitions as described above) at the C-terminus.

2. The method of claim 1, wherein the peptide or glycopeptide having a protected amino group at the N-terminus and a carboxyl group at the C-terminus is a peptide synthesized by solid-phase synthesis.

3. The method of claim 1, wherein the peptide has a length of 2 to 50 amino acid residues.

4. The method of claim 1, wherein the protecting group for the amino group is 9-fluorenylmethyloxycarbonyl (Fmoc), t-butyloxycarbonyl (Boc), or benzyloxycarbonyl (Cbz).

5. The method of claim 1, wherein the base used in steps (1) to (3) is a tertiary amine or an inorganic base.

6. The method of claim 1, wherein the compound represented by the formula R—SO$_2$—N=C=O is p-toluenesulfonyl isocyanate.

7. The method of claim 1, wherein the compound represented by the formula Hal-CH$_2$—X is iodomethane (CH$_3$I) or iodoacetonitrile (ICH$_2$CN).

8. The method of claim 1, wherein the compound represented by Y—SH is benzyl mercaptan, HS(CH$_2$)$_9$COOCH$_3$, or HSCH$_2$P(C$_6$H$_5$)$_2$.

9. The method of claim 2, wherein the peptide has a length of 2 to 50 amino acid residues.

10. The method of claim 2, wherein the protecting group for the amino group is 9-fluorenylmethyloxycarbonyl (Fmoc), t-butyloxycarbonyl (Boc), or benzyloxycarbonyl (Cbz).

11. The method of claim 3, wherein the protecting group for the amino group is 9-fluorenylmethyloxycarbonyl (Fmoc), t-butyloxycarbonyl (Boc), or benzyloxycarbonyl (Cbz).

12. The method of claim 9, wherein the protecting group for the amino group is 9-fluorenylmethyloxycarbonyl (Fmoc), t-butyloxycarbonyl (Boc), or benzyloxycarbonyl (Cbz).

* * * * *